US008815283B2

(12) United States Patent
Stover et al.

(10) Patent No.: US 8,815,283 B2
(45) Date of Patent: Aug. 26, 2014

(54) IMMUNO-COMPATIBLE HYDROGEL SYSTEM

(75) Inventors: Harald Stover, Dundas (CA); Nicholas Burke, Dundas (CA); Casey Mills, Hamilton (CA)

(73) Assignee: McMaster University, Hamilton, Ontario (CA)

( * ) Notice: Subject to any disclaimer, the term of this patent is extended or adjusted under 35 U.S.C. 154(b) by 0 days.

(21) Appl. No.: 13/375,267

(22) PCT Filed: Jun. 2, 2010

(86) PCT No.: PCT/CA2010/000830
§ 371 (c)(1),
(2), (4) Date: Jan. 18, 2012

(87) PCT Pub. No.: WO2010/139061
PCT Pub. Date: Dec. 9, 2010

(65) Prior Publication Data
US 2012/0107394 A1 May 3, 2012

Related U.S. Application Data

(60) Provisional application No. 61/213,367, filed on Jun. 2, 2009.

(51) Int. Cl.
*A61K 9/48* (2006.01)
*A61K 9/00* (2006.01)

(52) U.S. Cl.
CPC .................................. *A61K 9/0024* (2013.01)
USPC ............. 424/451; 424/487; 424/93; 514/772

(58) Field of Classification Search
CPC ....................................................... A61K 9/24
USPC .................................. 424/451, 486; 514/772
See application file for complete search history.

(56) References Cited

U.S. PATENT DOCUMENTS 6,630,243 B2 * 10/2003 Valint et al. ................... 428/420
2005/0147594 A1 7/2005 Leblond et al.

FOREIGN PATENT DOCUMENTS

WO 2003/094898 11/2003
WO 2009/124388 10/2009

OTHER PUBLICATIONS

Mazudmer et al., "Self-cross-Linking Polyelectrolyte Complexes for Therapeutic Cell Encapsulation", Biomacromolecules, 2008, 9, pp. 2292-2300; published Jul. 30, 2008 by American Chemical Society.*
Mazumder et al., title: Core-cross-linked alginate microcapsules for cell encapsulation; Biomacromolecules, vol. 10 (6), pp. 1365-1373; published online Apr. 27, 2009 by American Chemical Society.*

(Continued)

*Primary Examiner* — Richard Schnizer
*Assistant Examiner* — Yanzhi Zhang

(57) ABSTRACT

An immuno-compatible hydrogel system is provided that is resistant to protein binding. The hydrogel system is prepared by contacting a hydrogel solution with a cross-linking agent to form a gel, exposing the gel to an aqueous solution comprising a first polyelectrolyte to form a polyelectrolyte-coated hydrogel, exposing the polyelectrolyte-coated hydrogel to a second polyelectrolyte to form a crosslinked matrix and exposing the matrix to conditions which eliminates, or at least reduces, protein binding sites on the matrix.

20 Claims, 2 Drawing Sheets

(56) References Cited

OTHER PUBLICATIONS

Kumar et al., "Innate Immune Response of Corneal Epithelial Cells to *Staphylococcus aureus* Infection: Role of Peptidoglycan in Stimulating Proinflammatory Cytokine Secretion"; Apr. 23, 2004.*

Gardner, et al., "Cross-linked Microcapsules Formed From Self-Deactivating Reactive Polyelectrolytes", Langmuir, 2010, 26(7), 4916-4924.

Mazumder, et al., "Self-Crosslinking Polyelectrolyte complexes for Therapeutic Cell Encapsulation", Biomacromolecules, 2008, 9, 2292-2300.

Mazumder, et al., "Core-Cross-Linked Alginate Microcapsules for Cell Encapsulation", Biomacromolecules, 2009, 10, 1365-1373.

Shen et al: "Mechanically enhanced microcapsules for cellular gene therapy", Journal of Biomedical Materials Research Part B: Applied Biomaterials, vol. 90B, No. 1, Dec. 17, 2008, pp. 350-361.

Thu et al: "Alginate polycation microcapsules. I. Interaction between alginate and polycation.", Biomaterials, vol. 17, No. 10, May 1, 1996, pp. 1031-1040.

Orive G et al: "Biocompatibility of alginate-poly-l-lysine microcapsules for cell therapy", Biomaterials, Elsevier Science Publishers BV., Barking, GB, vol. 27, No. 20, Jul. 1, 2006, pp. 3691-3700.

\* cited by examiner

IMMUNO-COMPATIBLE HYDROGEL SYSTEM

FIELD OF THE INVENTION

The present invention relates to immuno-compatible hydrogel systems.

BACKGROUND OF THE INVENTION

Immunoisolation and transplantation of primary or genetically engineered cells of allo- or xenogenic origin holds great potential to treat many hormone and enzyme deficiency disorders. The principle application of the technology has been the treatment of a wide variety of endocrine disease, including diabetes mellitus, hypoparathyroidism, dwarfism, central nervous system diseases, including Parkinson's, Alzheimer's, ALS, other genetic disorders including lysosomal storage disorders (LSDs), hemophilia as well as other conditions like kidney and/or liver failure and cancer.

The basic idea of microencapsulation is to entrap cells in a semi-permeable polymeric hydrogel and implant them into the body where, ideally, they remain undetected by the immune system for as long as possible. Often, the hydrogel alone is too permeable, so it is coated with a thin permeability-controlling shell. The most common type of microcapsule is the alginate-poly-L-lysine (PLL)-alginate (APA) capsule. An APA capsule consists of a calcium-alginate hydrogel core, surrounded by PLL (a polycation) and a final coating of alginate (a polyanion). The major advantages to using alginate are that it is processable at physiological conditions, and it does not interfere with cellular function.

However, the inconsistencies associated with alginate (a naturally occurring polysaccharide, composed of varying amounts of β-D-manuronic (M) and α-L-guluronic (G) acids, when isolated from different sources and purified by different procedures, is a major disadvantage. In terms of an immune response, alginate has been shown to contain variable amounts of inflammatory or immunogenic proteins, polyphenols and endotoxins. These compounds may cause fibrotic overgrowth around the capsule, leading to cell asphyxiation. In terms of mechanical strength, capsule failure after transplantation has been attributed to weakening of the calcium-alginate core caused by exchange of calcium for sodium in the body, followed by core swelling and rupture of the immuno-isolating outer shell. As well, alginate has recently been reported to degrade by oxidative-reductive and hydrolytic processes in the body, raising further concerns about long-term applications. At best, alginate varies with harvest location and harvesting methods, and requires substantial purification to be acceptable for human use.

To improve APA capsules, synthetic polymers have been utilized with varying degrees of success. The use of synthetic polymers permits manipulation to alter polymeric properties and avoids residual biological impurities found in naturally occurring polymers. A diversity of covalent modifications utilizing synthetic polymers have been used to improve the mechanical and chemical stability, permeability, and biocompatibility of APA microcapsules. In this regard, polymer-bound reactive groups have been utilized which are typically less toxic, for example, covalent cross-links throughout a linear pluronic polymer (a triblock copolymer of poly(ethylene glycol) and poly(propylene glycol)) hydrogel core, using Michael-type addition between pluronic chains having thiol and acrylate end groups have been used, as well as microcapsules that form covalent bonds through photodimerization of modified poly(allylamine) or PLL in the capsular membrane. The use of a reactive polyanion-bearing acetoacetate groups that form covalent crosslinks with poly-L-lysine has also been described.

However, there remains a need to provide an improved hydrogel system which overcomes or at least reduces the disadvantages of existing systems, for example, immunological incompatibility, including for example, undesirable binding to endogenous proteins. In particular, existing crosslinking systems tend to contain residual functional groups even after crosslinking, and these may subsequently bind proteins or undergo other undesirable reactions.

SUMMARY OF THE INVENTION

An immuno-compatible hydrogel system is provided herein comprising a crosslinked polymer matrix which is resistant to protein binding.

Accordingly, in one aspect of the present invention, a hydrogel system is provided comprising a covalently crosslinked polymer matrix, wherein said matrix is essentially resistant to protein binding.

In another aspect, a method of making an immunocompatible hydrogel system is provided. The method comprises the steps of:
  i) contacting a hydrogel solution with a cross-linking agent to form a gel;
  ii) exposing the gel to an aqueous solution comprising a first polyelectrolyte to form a polyelectrolyte-coated hydrogel;
  iii) exposing the polyelectrolyte-coated hydrogel to a second polyelectrolyte suitable to react with said first polyelectrolyte to form a covalently crosslinked matrix; and
  iv) exposing the matrix to conditions which eliminates, or at least reduces, protein binding sites on the matrix.

These and other aspects of the invention will become apparent in the detailed description that follows and by reference to the figures.

DETAILED DESCRIPTION OF THE INVENTION

Figure 1:
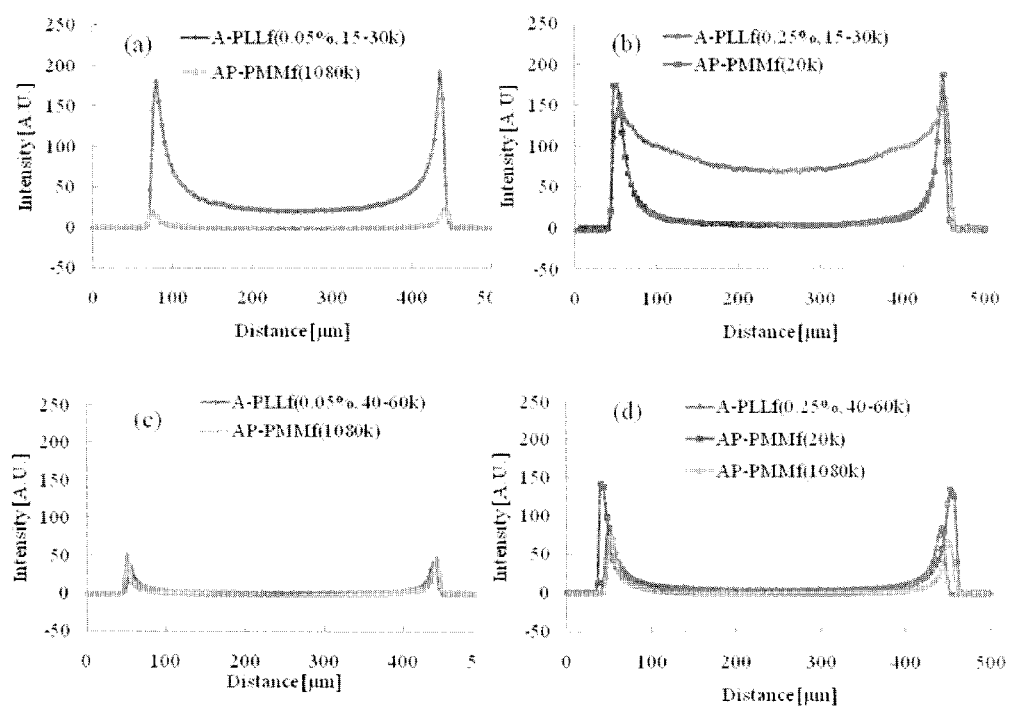
FIG. 1 illustrates line profiles from confocal images of hydrogel capsules comprising varied compositions of polyanion and polycation.

An immuno-compatible hydrogel system is provided comprising a covalently crosslinked polymer matrix that essentially lacks protein binding sites, and is therefore essentially resistant to protein binding.

The term "hydrogel" generally refers to water soluble polymer systems capable of being gelled using biocompatible means such as divalent cation binding and thermal gellation, and includes, for example, calcium alginate, barium alginate, agarose and hydrogel systems such as those described in Prokop et al. (Adv Polym Sci 1998, 136, 1-51 and 53-73), the contents of which are incorporated herein by reference, for example alginate-cellulose sulphate hydrogel mixtures gelled in calcium chloride/polymethylene-co-guanidine.

The term "immuno-compatible" refers to hydrogel systems which do not induce an immune response on administration to a host, e.g. exhibit reduced binding with endogenous host proteins. Thus, the present hydrogel system lacks protein-binding sites, e.g. reactive sites capable of binding with surrounding proteins, within the crosslinked polymer matrix. Reactive groups (e.g. anhydrides, reactive esters (N-hydroxysuccinimidyl, pentafluorophenyl), azlactones) on the hydrogel system are converted into unreactive groups to reduce the possibility of undesired protein binding that could otherwise cause or contribute to a deleterious immune response to the hydrogel on transplant. The term "lacks" or "essentially lacks" is used herein to mean that the polymer matrix exhibits a negligible or insignificant amount of reactive protein binding sites, e.g. less than about 1% the original reactive protein binding sites remain.

The term "covalently crosslinked" as used herein with respect to a polymer matrix refers to the formation of covalent bonds between reactive polymers within a hydrogel which are stable in the presence of an ionic solution (e.g. a sodium chloride solution at a concentration of about 1-2 M), or at high pH levels, e.g. pH 12-13, such as in the presence of 0.1 N sodium hydroxide. This is in contrast to electrostatic interactions which are commonly labile in the presence of such ionic solutions, and at high pH.

The present hydrogel system may be prepared using a water soluble polymer capable of being gelled using biocompatible means such as divalent cation binding, for example, calcium alginate and barium alginate, and thermal gellation. Other high viscosity gel-forming polymers such as cellulose sulphate may be used instead of alginate, or together with alginate, to form the primary hydrogel core. Ionic gelling agents suitable for this purpose include calcium chloride or barium chloride.

The resulting gel, for example in the form of beads or capsules, may then be coated with a first biocompatible polyelectrolyte, such as a polycation, to form a hydrogel-polyelectrolyte complex, e.g. a sodium alginate-polycation solution. Suitable polycations for this purpose include those having a molecular weight and charge density suitable for electrostatic binding to the hydrogel, as well as a sufficient quantity of reactive groups, e.g. primary or secondary amines, to participate in a subsequent crosslinking step. The appropriate molecular weight of a first polyelectrolyte will depend on the nature of the hydrogel, including composition, concentration and pore size of the hydrogel, as well as on the nature of the second polyelectrolyte, including its molecular weight. Accordingly, suitable polycations for use as the first electrolyte include those having a molecular weight that permit their diffusion into the hydrogel core, for example, having a molecular weight in the range of about 1-200 kDa, preferably 2-100 kDa, such as 4-15 kDa, and 15-30 kDa, and 30-60 kDa, including homopolymers and copolymers based on monomers having primary amine groups such as aminoethyl methacrylate, aminopropylmethacrylamide, aminoethyl acrylate, allylamine, vinylamine and related monomers. It may be advantageous to use copolymers of amine-containing monomers with 25 to 75 mol % of uncharged hydrophilic comonomers such as hydroxyethyl methacrylate or hydroxypropylmethacrylamide, in order to reduce the positive charge density and thereby reduce inflammatory responses on implantation of the system into a host, such as by electrostatic binding of proteins. Other suitable polyamines include polymers such as poly-L-lysine, chitosan, polyornithine and polyethyleneimine.

The amount of the first polyelectrolyte appropriate for inclusion in the system is an amount that does not adversely affect the mechanical properties of the hydrogel core while being an amount that will result in sufficient covalent crosslinking on addition of a second reactive polyelectrolyte to the hydrogel, e.g. a polyelectrolyte that is capable of crosslinking with the first polyelectrolyte, for example, an amount that results in at least about a 1:1 stoichiometric functional group ratio between the first polyelectrolyte and the second polyelectrolyte. In one embodiment, a concentrated alginate hydrogel bead dispersion is exposed to three times its volume of a polycation as the first electrolyte at concentrations of about 0.02-1%, preferably 0.05 to 0.5, and most preferably 0.1 to 0.2 weight/vol % solution of polycation in aqueous saline or an aqueous solution containing both sodium chloride and calcium chloride. It is understood that these ratios may vary with the diameter and porosity of the hydrogel beads and possibly other factors such as the molecular weight, composition and amount of polyelectrolyte loaded onto the bead.

Following coating of the hydrogel with a first selected polyelectrolyte, e.g. a polycation, the hydrogel is then coated with a second polyelectrolyte, e.g. a polyanion, that is reactive with the first polyelectrolyte to covalently crosslink with the first polyelectrolyte. Suitable polyanions for use as the second polyelectrolyte (where the first polyelectrolyte is a polycation) have a molecular weight in the range of about 10 to 2000 kDa, more preferably in the range of 20 to about 1080 kDa, and most preferably in the range of 20 to about 500 kDa. Thus, examples of suitable polyanions include polyanions comprising reactive groups such as anhydride groups. Thus, suitable polyanions and precursors that become polyanions upon partial hydrolysis, include copolymers of maleic anhydride, cyclic anhydrides such as itaconic anhydride and citraconic anhydride, and linear anhydrides such as methacrylic anhydride, with comonomers that facilitate the polymerization thereof such as alkyl vinyl ethers, e.g. methyl vinyl ether and ethyl vinyl ether, and olefins such as ethylene and propylene. Copolymers of azlactones such as vinylazlactones, e.g. 2-vinyl-4,4'-dimethylazlactone with acrylic comonomers such as acrylic acid, methacrylic acid, and optionally a third neutral comonomer such as hydroxyethyl methacrylate or hydroxypropylmethacrylamide, are also appropriate polyanions, as are copolymers of N-acryloxysuccinimide, N-methacryloxysuccinimide or glycidyl methacrylate, with anionic comonomers such as acrylic comonomers and a third optional neutral comonomers.

The second polyelectrolyte may also be a neutral copolymer that is reactive with the first polyelectrolyte. Thus, neutral copolymers that are reactive with a polycation include, for example, those formed by copolymerization of electrophilic monomers selected from the classes of vinylazlactones, e.g. 2-vinyl-4,4'dimethylazlactone, succinimides, e.g. N-acryloxysuccinimide or N-methacryloxysuccinimide, and other strained ring-containing monomers such as glycidyl methacrylate, with neutral hydrophilic comonomers such as hydroxyethyl methacrylate, methoxypolyethyleneglycolmethacrylate, and acrylamide.

The amount of second polyelectrolyte appropriate for inclusion in the system is an amount that does not substantially affect the properties of the hydrogel while being an amount that results in sufficient covalent crosslinking with the first polyelectrolyte, for example, an amount in the range of about 3 times the volume of the hydrogel dispersion, with concentrations of second polyelectrolyte (or neutral equivalent) in the range of 0.01 to 1%, and preferably 0.03 to 0.3%. If polyanions of sufficiently high molecular weight, for example a molecular weight of at least about 250 kDa, or sufficiently high viscosity are used (for example, a viscosity of at least about 30 cps, and preferably higher), these polyanions may themselves serve as the hydrogel precursor as well as the polyanion.

As one of skill in the art will appreciate, the first polyelectrolyte may either be a suitable polycation or polyanion, and similarly, the second polyelectrolyte may either be a polyanion or a polycation. However, in order for covalent crosslinkages to occur, the first and second polyelectrolytes cannot both be polyanions or both be polycations. In cases where the first polyelectrolyte is a polyanion and the second polyelectrolyte is a polycation, it may be desirable to expose the hydrogel to an additional polyanion coating. In this regard, a small amount of a biocompatible polycation such as chitosan or a synthetic analog may be combined with the primary hydrogel in order that a single exposure to reactive polyanion would lead to the desired crosslinked network.

Cross-linking between the first and second polyelectrolytes may occur externally to form an outer shell on the hydrogel, e.g. the outer layer or surface of the hydrogel which may generally be about 1-100 micrometer in thickness, e.g. 1-50 micrometer in thickness. Some cross-linking between first and second polyelectrolytes may also occur within the hydrogel core, e.g. internal to the outer shell of the hydrogel, depending on the characteristics of each of the polyanion and polycation. For example, polyelectrolytes having a molecular weight of less than about 100 kDa, e.g. less than about 50 kDa, may also crosslink internally.

To provide a hydrogel system with enhanced mechanical properties, it may be desirable to prepare the hydrogel with additional first and second polyelectrolyte coatings as described above in order to yield an outer cross-linker shell of greater thickness, e.g. greater than 50 micrometers in thickness, higher density or greater cross-link density.

It may be desirable to provide a detectably labeled hydrogel system in order to render it trackable following its administration to a mammal, e.g. in the transplant of cells. In this regard, electrophilic reactive groups such as anhydride groups in the polyanion, may be labelled with a marker, such as a fluorescent marker, e.g. amino fluorescein, or may be modified to incorporate a chemical or biological modifier to otherwise enhance the function of the hydrogel system, for example to enhance the viability of encapsulated cells or the biocompatibility of the crosslinked network. Examples of suitable modifications include the incorporation of poly(ethylene glycol) groups by reaction of the initial polyanhydride with amino-poly(ethylene glycol), the incorporation of adhesion peptide sequences such as RGD, a tripeptide sequence consisting of arginine-glycine-aspartate, and the incorporation of spacers or other functionalities. Markers or modifiers may be added to the polyanion prior to its application to the hydrogel to engage in crosslinking.

In order to optimize the immuno-compatibility of the present crosslinked hydrogel, the hydrogel is further treated to eliminate residual reactive groups in the layers containing the second electrolyte, e.g. electrophilic groups of a final polyanion coating, or nucleophilic groups on a final polycation coating. The nature of this treatment will depend on the nature of the residual reactive group to be eliminated or converted to an unreactive group. Preferably, the treatment is a biocompatible treatment to ensure that the biocompatibility of the hydrogel system is not jeopardized. Thus, reactive electrophilic groups on polyanions may be converted on treatment with, for example, cytocompatible amines, such as aminoethanol or amino sugars, to form less reactive amide groups. Reactive anhydrides and other electrophilic reactive groups may also be converted to less reactive groups by hydrolysis. In this regard, a second reactive polyelectrolyte containing a large number of reactive groups may be exposed to a reaction to reduce the number of reactive entities and thereby yield a polyelectrolyte that retains the capacity to crosslink on a hydrogel coated with a first electrolyte, e.g. retain a sufficient number of reactive groups in order to undergo effective crosslinking. For example, a polyanion for use as the second polyelectrolyte may undergo partial hydrolysis in the presence of water to form a polyanion with a reduced number of reactive electrophilic groups, but still retaining a sufficient number of reactive electrophilic groups to undergo crosslinking with polycation deposited on a hydrogel. Residual electrophilic reactive groups that are not consumed in the crosslinking reaction with the polycation may subsequently hydrolyze on their own account, to form less reactive groups such as carboxylate anions.

The treatment or reaction to essentially eliminate or convert residual reactive groups on the hydrogel to less reactive groups may be conducted in the presence of facilitating agents. For example, the use of hydrolysis to convert residual reactive groups to less reactive groups may be facilitated by hydrolysis catalysts including certain enzymes, such as esterases, as well as tertiary amines.

In addition, the polymers (polyanions or polycations) may be modified to customize the properties of hydrogel system. For example, the polymer may be modified to introduce macromolecules having a desirable property, including anti-inflammatory cytokines (such as IL-10 and IL-2a), molecules which function to inhibit non-specific protein binding (e.g. amino-polyethylene glycol) or other regulatory proteins. This modification may be carried out prior to deposition of the reactive polyanion onto the polycation-coated calcium alginate beads (or deposition of polycation onto polyanion-coated beads). It may alternatively be carried out following deposition of polyanion onto the polycation-coated calcium alginate beads, provided that care is taken to ensure that sufficient reactive groups remain present on the crosslinked shell.

The present method, thus, yields a covalently crosslinked immuno-compatible hydrogel system with a reduced capacity to interact with proteins, e.g. a system that essentially lacks reactive protein binding sites (comprises less than 1% reactive protein binding sites) and, thus, is resistant to interactions with host proteins. The cross-linked polymer matrix also functions to stabilize the system, rendering it resistant to both chemical and mechanical challenges, thereby resulting in a hydrogel system having extended implant life in a host.

The present hydrogel system has widespread utility. At the outset, the cross-linked hydrogel system per se provides a stable, biocompatible, semi-permeable membrane. Among other utilities for such membranes, that would be well-known to those of skill in the art, an immuno-compatible crosslinked hydrogel membrane in accordance with the invention is useful in biomolecular separation techniques such as ion exchange and size exclusion chromatography. In this regard, it is noted that this system is not limited to the formation of beads and/or capsules, but may also be prepared as sheets of hydrogel by spin coating or deposition on a flat surface using a spreading knife, gelling using calcium chloride and crosslinking by exposure to the reactive polyamine. In this way, sheets consisting of covalently crosslinked polymer, with or without a target particle, may be prepared. In such applications, it is also possible to avoid use of alginate, and form crosslinked networks from only a bead, string or sheet of the reactive polyanion exposed to polycation.

The present hydrogel system is also useful as a biocompatible/immuno-compatible coating on devices for implant, including, for example, stents, catheters, other medical implants and the like.

Additionally, the present immuno-compatible hydrogel system is useful as an encapsulation system for use to transplant cells for the treatment of disease, such as lysosomal storage disease (LSD), diabetes, cancer or degenerative disease such as Parkinson's, and other conditions requiring cell transplant, or to deliver other encapsulated entities to a host, including for example, therapeutic agents, enzymes and hormones. In this regard, encapsulation of a target entity may be achieved by combining the entity with the hydrogel system during the polyelectrolyte coating steps. In this regard, it is noted that the present hydrogel system may be customized in order to provide a covalently crosslinked polymer network to retain the target entity, e.g. customized to have an average pore size that exceeds the size of the target.

Embodiments of the invention are described by reference to the following specific example which is not to be construed as limiting.

EXAMPLE 1

PMM50 Crosslinked Alginate Capsules

Materials:
Poly(methyl vinyl ether-alt-maleic anhydride) (PMM), as purchased (20 kDa) from Scientific Polymer Products, Ontario, N.Y.; 1080 kDa from Sigma-Aldrich, Oakville, ON) were found to be partly hydrolyzed, and were hence heated in a vacuum oven at 140° C. for 5 days to reform to anhydride copolymer, $PMM_0$, with less than 0.5% hydrolysis as determined by $^1$H-NMR. The fully hydrolyzed analog $PMM_{100}$ (216 kDa), 5-aminofluorescein (AF), poly(L-lysine hydrobromide) (PLL, 15-30 kDa and 40-60 kDa), tetramethylrhodamine isothiocyanate-conjugated bovine serum albumin (BSAr, 66 kDa, 1 mol TRITC per mol albumin), fluorescein isothiocyanate-conjugated dextran (10, 70, 150, 250 and 500 kDa), HEPES sodium salt, acetonitrile-$d_3$ (99.96 atom % D), $D_2O$ (99.99 atom % D) and trypan blue stain (0.4% in 0.81% aqueous NaCl) were purchased from Sigma-Aldrich, Oakville, ON, and used as received. Sodium alginate (Pronova UP MVP batch no. FP-610-03) was purchased from Novamatrix, Norway. Sodium chloride and N,N-dimethylformamide (reagent, DMF) (Caledon Laboratories Ltd, ON), and calcium chloride (minimum 96% powder, anhydrous, Sigma-Aldrich, ON) were used as received. Sodium hydroxide and hydrochloric acid solutions were prepared from concentrates (Anachemia Chemical, Rouses Point, N.Y.) by diluting to 0.100 M or 1.000 M with deionized water.

Preparation of $PMM_{50}$ and $PMMf_{50}$ by Controlled Hydrolysis of $PMM_0$ $PMM_0$ (100 mg) was dissolved in 1.0 mL of an acetonitrile-$d_3$/$D_2O$ (9:1 v/v) mixture in a screw-cap glass vial, forming a 10 w/v % solution. The vial was placed in an oven set to 60° C. for either 14.5 hrs (20 k $PMM_0$) or 17 hrs (1080 k $PMM_0$). Reaction times were determined by $^1$H-NMR to result in 50% hydrolysis, forming $PMM_{50}$(20 kDa or 1080 kDa), respectively. At room temperature, 0.2 ml of the reaction mixture was diluted to 10 mL with 35 mM HEPES pH 7.8 buffered saline. The resulting slightly turbid solution was immediately agitated on a vortex mixer for 10-30 sec (at which point the solution was clear), and then quickly filtered (0.45 μm), to give a final aqueous coating solution containing 0.2 wt % $PMM_{50}$. The complete dilution/agitation/filtration sequence was completed within 1 minute in order to minimize hydrolysis, and the solution was immediately used for coating. Coating solutions containing 0.2 wt % of the fluorescently labeled analog $PMMf_{50}$, were prepared in the same way, except that 2 mol % AF (relative to total anhydride) was added at the beginning of the $PMM_0$ hydrolysis in acetonitrile.

The degree of labeling for $PMMf_{50}$ (20 k and 1080 k) was determined by dialyzing fully hydrolyzed $PMMf_{100}$ against deionized water for one week, with daily water changes, using cellulose dialysis tubing with a molecular weight cut-off of 14,000 Da (Membra-cel, Viskase, Darien, Ill.) until the dialysate showed no signals for AF by UV-Vis spectroscopy. The polymer was then isolated by freeze-drying. The degree of labeling was found to be 1.03 and 0.88 mol % for $PMMf_{50}$ of 20 kDa and 1080 kDa, respectively.

Preparation of FITC-Labelled Poly(L-Lysine) (15-30 and 40-60 kDa).

FITC-labelled poly(L-lysine), PLLf, was prepared as described earlier (Mazumder et al. 2008. Biomacromolecules 9, 2292-2300. the relevant contents of which are incorporated herein by reference). For example, PLL (15-30 kDa, 100 mg, 0.48 mmol lysine.HBr units) was dissolved in 10 mL of 0.1M $NaHCO_3$ buffer (pH 9) in a 20 mL glass vial. FITC (2.0 mg, 0.005 mmol) dissolved in 0.2 mL DMF was added to the PLL solution and the mixture was stirred for 90 min at 20° C. The resulting solution was adjusted to pH 7 with 1 M HCl and then dialysed for 5 days in deionized water using cellulose tubing (Spectrum Laboratories, 3.5 kDa MW cut-off) with daily water changes until the dialysate showed no absorbances for DMF or fluorescein. PLLf (15-30 kDa) was isolated by freeze-drying. Yield: 68.5 mg. The labelling degree was determined to be 1.05 mol % by UV-visible spectroscopy (73000 $M^{-1}$ $cm^{-1}$) in 25 mM HEPES buffer (pH 7.4).

PLLf (40-60 kDa) was prepared in a similar manner from PLL (40-60 kDa, 202.8 mg, 0.97 mmol) in 18 mL of 0.1M $NaHCO_3$ buffer (pH 9) and FITC (3.7 mg, 0.0095 mmol) in 0.37 mL DMF except that dialysis tubing with a 14 kDa MW cut-off (Membra-Cel, Viskase Corp., Darien, Ill.) was used. Yield: 148.2 mg. Labelling degree: 0.85%.

Standard Procedure for Formation of Alginate-PLL-$PMM_{50}$ Capsules (AP-$PMM_{50}$)

All capsules were prepared by a procedure described previously (Sun, 1988. Methods Enzymol. 137, p 575, the relevant contents of which are incorporated herein by reference). Briefly, a 1.0 wt % sodium alginate solution in aqueous saline was filtered (0.45 μm) and extruded through a 27 gauge needle at a liquid flow rate of 0.5 mL/min into a gellation bath containing 1.1 wt % calcium chloride and 0.45 wt % sodium chloride. The resulting calcium alginate beads were washed once with fresh gelling bath solution, followed by a saline wash. The alginate beads were then coated with PLL (15-30 or 40-60 kDa, both at 0.05 and 0.25 wt %) for 6 min. The resulting AP capsules were washed twice with saline, and coated with a 0.2% $PMM_{50}$ (20 kDa or 1080 kDa) solution for 6 min at 10° C., followed by a saline wash. All coating and washing steps involved a 3:10 volume ratio of concentrated bead suspension to coating or saline wash solution. Table 1 identifies the various compositions prepared.

TABLE 1

| Name | A-PLL (wt %, MW) | $PIMM_{50}$ (MW) | Shell Thickness (full width at ½ height of confocal microscopy line profile)[μm] | max height of line profile [A.U.] |
|---|---|---|---|---|
| [1] | A-PLL(0.05%, 15-30k) | $PMM_{50}$(1080k) | 13.4 | 20 |
| [2] | A-PLL(0.05%, 15-30k)* | $PMM_{50}$(1080k)* | 13.0 | 47 |
| [3] | A-PLL(0.25%, 15-30k) | $PMM_{50}$(20k) | 14.8 | 161 |
| [4] | A-PLL(0.05%, 40-60k) | $PMM_{50}$(1080k) | 10.2 | 41 |

TABLE 1-continued

| Name A-PLL (wt %, MW) | PIMM$_{50}$ (MW) | Shell Thickness (full width at ½ height of confocal microscopy line profile)[μm] | max height of line profile [A.U.] |
|---|---|---|---|
| [5] A-PLL(0.25%, 40-60k) | PMM$_{50}$(1080k) | 11.0 | 71 |
| [6] A-PLL(0.25%, 40-60k) | PMM$_{50}$(20k) | 12.6 | 139 |

All microcapsules were made from 1% alginate solutions, all coating solutions are in 0.9% NaCl, all PMM$_{50}$ coating solutions were 0.2 wt %.
*These are four-layer capsules A[PLL(0.05%, 15-30k)-PMM$_{50}$]$_2$, preparation details described below.

Standard Procedure for Formation of A[P(0.05, 15-30 k)-PMM$_{50}$]$_2$

Analogous four-layer capsules were prepared by coating Ca-Alg cores with, in sequence, PLL (0.05%, 15-30 kDa) for 6 min, PMM$_{50}$ (0.2%, 1080 kDa) solution for 4 min, PLL (0.05%, 15-30 kDa) solution for 6 mins, and PMM$_{50}$ (0.2%, 1080 kDa) solution for 6 min, with two saline washes after each PLL coating and after the final PMM$_{50}$ coating, and one saline wash after the first PMM$_{50}$ coating.

PMM Calibration Curve

Appropriate amounts of fully hydrolyzed poly(methyl vinyl ether-alt-maleic anhydride), PMM$_{100}$ were dissolved in 35 mM HEPES pH 7.8 buffered saline, to mimic the amount of carboxylic acid groups present in a 0.2% PMM solution with degrees of hydrolysis of 100, 80, 60, 50, 40 and 20%. The pH of these solutions were measured and used to generate a pH vs. % hydrolysis calibration curve.

Characterization:

Proton NMR spectra were obtained on a Bruker AV200 spectrometer. The pH of aqueous solutions was measured on a Corning 440 pH meter. Rates of hydrolyses in aqueous saline were measured using a PC-Titrate (Mandel Scientific) automatic titrator.

Capsules were examined by optical and fluorescence microscopy with an Olympus BX51 optical microscope fitted with a Q-Imaging Retiga EXi digital camera and ImagePro software. Capsules were also examined using a ZEISS LSM 510 confocal laser scanning microscope (CLSM) fitted with air-cooled Argon and HeNe lasers (LASOS; LGK 7628-1), and running LSM Image browser software (version 3.5). Images were further analyzed with ImageJ software to generate 10 pixel wide line profiles.

Kinetic Permeability Study:

Capsule permeability was evaluated using fluorescein-labeled dextrans of 10, 70, 150, 250 and 500 kDa. For each dextran, approximately 20 AP-PMM$_{50}$ capsules were placed on a microscope slide in the centre of a Teflon washer (1.5 cm diameter, 300 μm high), exposed to 200 μL of 0.1% dextran-FITC in saline, promptly covered with a glass cover slip and examined by fluorescence microscopy. This procedure, described recently (Gardner et al.) flattens and seals the top and bottom surfaces of the beads, transforming them into rounded cylinders that permit observation of lateral in-diffusion of the labeled dextran. Images were taken every minute for 20 min and the fluorescence intensities from the central ca. 20% of the beads, as well as from the surrounding continuous phase, were obtained using the ImagePro software. Reported intensity values are the ratio of intensity of the bead centre to the continuous phase, in order to minimize effects of photobleaching. These permeability measurements were carried out in triplicate for each MW of dextran.

Permeability by Confocal Microscopy:

In-diffusion of fluorescently-labelled dextran was also studied using a method involving a 24 h incubation of 0.2 g of microspheres in 0.0015% dextran solutions, followed by measurement of fluorescence intensity profiles across equatorial confocal microscopy sections using ImageJ software and 10 pixel wide line profiles.

Test for Covalent Crosslinking

Capsules made with a fluorescently-labeled PMMf were used to test for crosslinking. One drop of concentrated capsule suspension containing about 30 capsules was placed on a microscope slide and viewed by fluorescence microscopy. The supernatant was removed and immediately replaced with 2 drops of 1 M sodium citrate, a good calcium chelator, and the capsules were gently mixed. This process was repeated once. Subsequently, the supernatant was replaced with two drops of 0.1 M sodium hydroxide under gentle agitation, and the integrity of any remaining shells assessed qualitatively.

Protein Binding Study

This procedure was carried out as described by Shen et al. J. Biomed. Mater. Res. B: Appl Biomater. 2009, the contents of which are incorporated herein by reference). Briefly, 0.1 mL of concentrated bead suspension was added to 1 mL of a 0.05% solution of rhodamine-labelled BSA (BSAr) in saline. After 24 h at room temperature, the capsules were washed five times with 1 mL saline for 2 min before examination by confocal microscopy for the presence and distribution of any residual BSAr.

Implantation Study

Calcium alginate capsules coated with crosslinked shells formed by deposition of PLL (0.1%, 15-30 k) and PMM50 (0.2%, 20 k) have been implanted into immune-competent mice for 6 days. The capsules were incubated in Dulbecco's Modified Eagle's medium (DMEM) for 2 days. Prior to implantation the cell culture medium was exchanged for saline. The animals were treated in accordance with Canadian Institutional Animal Care guidelines. C57BL/6 mice (Charles River, Montreal QC) were anaesthetized with isofluorane (Anaquest, Mississauga, Ontario) before a suspension of 3 mL microcapsules in normal saline (total volume 5 mL) was implanted into the intraperitoneal cavity of mice under sterile conditions using a 20 gauge catheter (BD, Oakville, ON). After six days the mice were sacrificed and the capsules were retrieved and examined by phase contrast microscopy.

Microcapsules containing cells were similarly implanted. A C2C12 mouse myoblast cell suspension was mixed with the sterile alginate solution to a final cell concentration of 2 million cells/mL of alginate. The alginate/cell mixture was gelled and the resulting beads coated by sequential exposure to PLL (0.1%/15-30 k or 0.05%/40-60 k) and PMM50 (0.2%/20 k). Following the final wash step, the microcapsules with cells were cultured in DMEM in a tissue culture incubator at 37° C. Prior to implantation the cell culture medium was exchanged for saline. The two types of capsules were implanted into immune-competent mice as described above.

Results

Calcium alginate beads were coated with PLL (15-30 kDa) and then a fluorescently labeled analog to PMM$_{50}$, PMMf$_{50}$. Confocal microscopy was used to confirm that PMMf$_{50}$ was bound to the capsule surface. With reference to Table 1, the full width at ½ height of the confocal microscopy line profiles is defined as the capsule thickness. All values have been calibrated to the same microscopy settings. Standard deviation (based on 6 values) is 2.5 µm or less for all width at ½ height values.

Line profiles from confocal images, as shown in FIG. 1, also suggest that only a small amount of PMMf$_{50}$ (1080 k) is actually bound to the surface. FIG. 1 illustrates line profiles of (a) [1] with reference to separate A-PLLf(0.05%, 15-30 k) capsules (b) [3] with reference to separate A-PLLf(0.25%, 15-30 k) capsules, (c) [4] with reference to separate A-PLLf (0.05%, 40-60 k) capsules, (d) [5] and [6] with reference to separate A-PLLf(0.25%, 40-60 k) capsules.

To confirm that the present shells involve covalent crosslinking in addition to the electrostatic linkages, the coated beads were exposed, in sequence to 1 M sodium citrate to chelate calcium and dissolve the calcium alginate hydrogel, and to 0.1 M sodium hydroxide to deprotonate PLL and break any electrostatic interactions. This method leaves only covalent crosslinks to preserve the structure of the shell. Capsules coated with PMMf$_{100}$, a material unable to form covalent crosslinks, deflated upon extraction of calcium with citrate but still showed distinct shells consisting of an A-P-PMMf$_{100}$ polyelectrolyte complex. When challenged with 0.1 M NaOH, the polyelectrolyte complex dissolved as PLL was deprotonated. Hollow shells resulted when AP-PMMf$_{50}$ capsules were treated with citrate. Subsequent exposure to sodium hydroxide revealed the presence of intact shells or shell fragments, reflecting the presence of covalent crosslinking in the shell. Treatment of AP-PMMf$_{50}$ 4-layer capsules with citrate followed by sodium hydroxide revealed the presence of more pronounced final shells indicating increased thickness and mechanical strength. This multi-layer approach, thus, provides an alternative method for improving capsule properties.

Optimization of AP-PMM$_{50}$ Capsules

A variety of AP-PMM$_{50}$ capsules were prepared in order to optimize the strength as measured by chemical challenges (citrate and sodium hydroxide). In these experiments, the type and concentration of alginate, polycation, and the degree of hydrolysis of PMM were kept constant, while varying the molecular weight and concentrations of both poly-L-lysine and PMMf$_{50}$, as well as the coating temperature. A-PLL (0.25%, 15-30 kDa)-PMM$_{50}$(0.2%, 20 kDa) capsules were found to have the greatest resistance to the chemical challenges, while acceptable resistance to chemical challenges was observed with a greater range of molecular weights and concentrations.

Encapsulation Temperature:

Most cell encapsulations are carried out at 4-10° C. in order to protect the cells by lowering their metabolic rate. Hence, coating of AP beads with PMM$_{50}$ was carried out at 10° C., as well as at room temperature. Many polymer properties, as well as the rates of hydrolysis and crosslinking, are temperature-dependent. The rate of hydrolysis should be lower at 10° C., allowing more time for coating and crosslinking, as well as leaving more anhydride groups to react with the amine groups of PLL. Measurements for both 20 k and 1080 k indicated that the rate of hydrolysis decreased slightly at 10° C. It was found that coating AP capsules with PMM$_{50}$ (1080 k) at 10° C. formed capsules that were no stronger than those made at room temperature. However, coating AP capsules with PMM$_{50}$(20 k) at 10° C. was found to improve the consistency and surface smoothness of the resulting AP-PMM$_{50}$ capsules. Therefore, subsequent coatings were carried out at 10° C.

Effect of PLL Molecular Weight and Concentration

The thickness and density of the crosslinked shells depend on the ability of the polyelectrolytes to diffuse into the calcium alginate matrix. In particular, lower MW PLL would be expected to diffuse further into the primary calcium alginate beads, and would give rise to thicker shells, provided the reactive polyanion can follow the polycation. As a first step, FITC-labelled poly-L-lysine, PLLf, of two different molecular weights and at two different concentrations, was coated onto calcium alginate beads, and the resulting distributions were studied by confocal fluorescence microscopy. FIGS. 1(a) and (b) shows that the lower MW PLLf, 15-30 kDa, penetrates significantly into the beads, both at low coating concentrations of 0.05% and especially at higher coating concentration (0.25%). Accordingly, a higher molecular weight PLLf (40-60 kDa) was used and found to penetrate much less into the beads, at either of the two concentrations used (0.05%; and 0.25%, FIGS. 1(c) and (d).

Effect of Matching Diffusion Properties for PLL and PMM$_{50}$.

AP beads made with either 15-30 k or 40-60 k PLL were coated with fluorescently-labeled PMMf to track the amount of PMMf bound and its distribution of the polyanion in the capsules. FIG. 1a and Table I indicate that high molecular weight PMMf$_{50}$(1080 kDa) was largely restricted to the outer shell of the capsule. To test whether lower molecular weight PMMf$_{50}$ could penetrate further into the beads, calcium alginate beads were exposed first to 0.25% PLL(15-30 kDa), which results in PLL being located throughout the bead, then to 0.2% PMMf$_{50}$(20 kDa). The line profile from the confocal image, shown in FIG. 1b, and the width at ½ height stated in Table 1, suggests that while PMMf$_{50}$(20 k) does not penetrate significantly further into the bead than its higher MW analog, PMMf$_{50}$(1080 k), substantially more PMM$_{50}$(20 k) is able to bind to PLL. In the case of PLL(40-60 k), the polycation is restricted to the surface but more is bound when higher coating concentrations are used (0.25% rather than 0.05%). The increased concentration of polycation at the surface allows for more PMM$_{50}$ binding (as seen in FIG. 1d), resulting in slightly stronger shells.

Permeability Studies on Optimized Capsule

Figure 2:
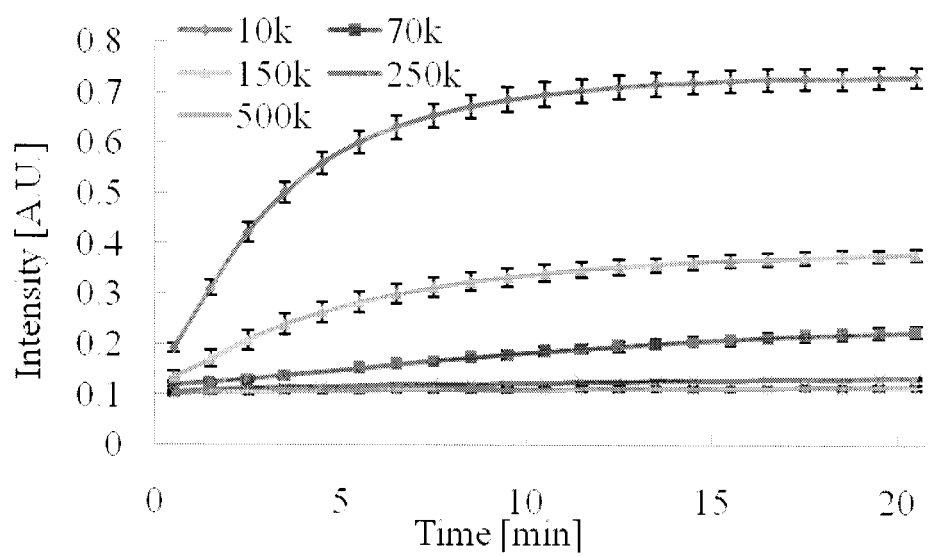
FIG. 2 graphically illustrates the extent of the lateral in-diffusion of dextrans of increasing molecular weight into hydrogel capsules according to an aspect of the invention.

To confirm that the thicker shell of the capsules of FIG. 1b still affords the permeability required for the cells' vitality in vivo, a kinetic permeability test as recently developed (Gardner et al. Langmuir, 2010) was used to measure the rate of in-diffusion of fluorescently labelled dextrans. FIG. 2 shows that 10 kDa dextran-FITC is able to diffuse rapidly into the capsules, reaching equilibrium within less than 10 minutes, suggesting that oxygen and small metabolites would rapidly pass through the exterior membrane. The 70 and 150 kDa dextrans diffuse at a much slower rate, and the 250 and 500 kDa dextrans are essentially excluded from the beads, suggesting that these crosslinked shells combine good permeability for low MW species with exclusion of high MW species, a desirable feature for materials designed for immuno-isolation. The apparent high rate of in-diffusion of the 150 kDa dextran is attributed to its extremely broad size distribution, which includes a significant amount of low MW chains.

Protein Binding Study on Optimized Capsule

One of the design points for the present PMM$_{50}$ type capsules was that the rapid hydrolysis of residual anhydride groups prevents covalent binding of protein during the incubation step commonly used after cell encapsulation. To test this, A-PLL(0.25%, 15-30 kDa)-PMM$_{50}$(0.2%, 20 kDa) beads were exposed to 0.05% BSAr for 24 hrs, followed by several saline washes. Subsequent confocal microscopy imaging showed no BSAr binding to the capsule shells, even with the detector gain set to its maximum. The absence of BSAr binding to the crosslinked shell indicates that no reactive anhydride groups remain on the capsule surface, and further that the hydrolyzed PMM does not bind BSAr electrostatically.

Implantation Studies of Empty Capsules Crosslinked with PLL/PMM50

Calcium alginate capsules coated with crosslinked shells formed by deposition of PLL (0.25%, 15-30 k) and PMM50 (0.2%, 20 k) were implanted into immune-competent mice for 6 days. After explantation, the recovered capsules were examined by phase contrast microscopy and showed minimal overgrowth, indicating the absence of significant immune response to these capsules.

Implantation Studies of Cell-Containing Capsules Crosslinked with PLL/PMM50

Microcapsules containing C2C12 mouse myoblast cell suspension and coated by sequential exposure to PLL (0.1%/15-30 k or 0.05%/40-60 k) and PMM50 (0.2%/20 k) were implanted into immune-competent mice. After one week, the recovered capsules showed minimal overgrowth (less than about 5%), indicating immune-protection of the encapsulated cells from the hosts' immune system. Phase contrast microscopy images of the recovered C2C12-containing capsules, either A-PLL(0.1%/15-30 k)-PMM(0.2%/20 k) or A-PLL (0.05%/40-60 k)-PMM(0.2%/20 k), reveal that the majority of explanted capsules are clear (greater than about 80%) and do not show any overgrowth associated with immune recognition of the transplanted capsules by the host's immune system.

EXAMPLE 2

PMV60 Crosslinker Alginate Capsules

Copolymers of 2-vinyl-4,4'-dimethylazlactone (VDMA, TCI America) with methacrylic acid (MAA, Aldrich) were prepared and used as an alternate reactive polyanion for the formation of covalently crosslinked shells around calcium alginate beads. A study of the reactivity ratios of these two monomers revealed reactivity ratios of 1.42 for VDMA and 0.42 for MAA, indicating that in a copolymerization VDMA gets incorporated preferentially. To compensate for this tendency, the copolymerization was carried out in semi-batch fashion such as to maintain a comonomer ratio of roughly 35 mol % VDMA:65 mol % MAA. This was done by starting with an initial comonomer ratio of 35 mol % VDMA to 65 mol % MAA, and adding sufficient VDMA at a decreasing rate during the copolymerization over the next two hours to approximately maintain this ratio. The copolymerizations were carried out in dimethyl sulfoxide (DMSO, anhydrous, Aldrich) as solvent at 70° C. for two hours, under nitrogen, and in the presence of one mol % azobis(isobutyronitrile) (Dupont) as radical initiator. The resulting polymer was isolated by precipitating the cooled reaction mixture into a tenfold excess of cold diethyl ether. Optionally, small amounts of tetrahydrofuran, in amounts not exceeding the volume of DMSO, can be added to the reaction mixture to improve precipitation behavior. The composition of the resulting copolymer was determined by proton NMR in DMSO-d6 and found to be 60 mole % VDMA and 40 mole % MAA. The molecular weight of the polymer was determined to be 66 kDa by aqueous gel permeation chromatography analysis of a fully hydrolyzed version of the polymer.

Poly((methacrylic acid-co-2-vinyl-4,4'-dimethylazlactone) [PMV60], containing 40% methacrylic acid and 60% 2-vinyl-4,4'-dimethylazlactone, is water-soluble at neutral pH due to the 40% methacrylic acid content. To ensure rapid polymer dissolution while minimizing hydrolysis of the azlactone groups, solid PMV60 was dissolved in a small amount of DMSO prior to the addition of 35 mM HEPES buffer (pH 7.8) in saline. The aqueous PMV60 solution containing about 5% DMSO has a pH of 7.4, which is the pH at which coating is performed. Deposition of PMV60 on calcium alginate beads coated with PLL leads to electrostatic attraction followed by covalent crosslinking in a manner analogous to that described for PMM50. The reactive azlactone groups react with the amine groups of PLL to form amide crosslinks. Residual azlactone groups on the PMV60 were found by potentiometric and NMR analysis to hydrolyze within about one day to form carboxylic acids. Capsule preparation, coating and testing as well as implantation studies were conducted essentially as described in Example 1 for PMM-coated capsules.

Model Capsule Formation:

Model capsules were formed by exposing calcium alginate beads to various concentrations of PLL (0.05 to 0.25% of 15-30 k or 40-60 k) and PMV60 (0.1 or 0.2%, 66 k) to form shell-crosslinked capsules resistant to citrate and sodium hydroxide challenges.

Implantation Studies of Empty Capsules Crosslinked with PLL/PMV60

Calcium alginate capsules coated with crosslinked shells formed by deposition of PLL (0.1%/15-30 k) and PMV60 (0.2%/66 k) were implanted into immune-competent mice for 6 days as described above for PMM50-coated capsules. After explantation, the recovered capsules showed minimal overgrowth, indicating absence of significant immune response to these capsules.

Implantation Studies of Cell-Containing Capsules Crosslinked with PLL/PMV60

Calcium alginate capsules containing C2C12 mouse myoblast cells, and coated with crosslinked shells formed by sequential exposure to PLL (0.1%/15-30 k) and PMV60 (0.2%/66 k) were implanted into immuno-competent mice for one week as described above for cell-containing capsules coated with PMM50. After explantation, the recovered capsules showed minimal overgrowth, indicating that good immune-protection of the encapsulated cells from the host's immune system. Phase contrast microscopy images of C2C12-containing capsules formed using PLL 15-30 k and coated with PMV60, explanted from the peritoneal cavity of immune competent mice after one week are clear and do not show any overgrowth associated with immune recognition of the transplanted capsules by the host's immune system.

CONCLUSION

A reactive polyanion formed by partially hydrolyzing poly (methyl vinyl ether-alt-maleic anhydride) was coated onto AP capsules to form a shell with covalent cross-links to the amino groups of PLL. Controlled hydrolysis of $PMM_0$ was performed in ACN-$d_3$/$D_2O$ and monitored by $^1H$ NMR. At 50% hydrolysis $PMM_{50}$ was diluted in a buffered saline solution, at which point hydrolysis was found to occur much more rapidly such that no anhydride groups would remain shortly after coating was completed. It was also shown that the distribution of the polyelectrolytes in the calcium alginate bead (amount bound, penetration depth into the hydrogel) depended on the MW of the PLL and PMM. The capsules formed with partially hydrolyzed $PMM_{50}$ comprised shells that withstood challenge to sodium hydroxide, unlike those formed with the fully hydrolyzed $PMM_{100}$, demonstrating that these shells were covalently crosslinked. During this process, it was found that higher concentrations PLL lead to stronger capsules that were better able to resist chemical challenges. Permeability studies showed that the covalently crosslinked shell formed around the AP-PMM capsules allowed for rapid in-diffusion of small molecules such as oxygen and metabolites while excluding larger MW species, such as immunoglobulins. The covalently crosslinked shell did not bind BSA, confirming that no remaining reactive anhydride groups are present following coating.

In addition, a reactive polyanion formed by semi-batch copolymerization of methacrylic acid with 2-vinyl-4,4'-dimethylazlactone, PMV60, was used in similar fashion to crosslink the outer layers of calcium alginate beads coated with PLL.

Both PMM50 and PMV60 crosslinked capsules, implanted into the peritoneal cavities of mice either with or without cells, showed little overgrowth following explantation after one week, indicating the successful isolation of the contained cells from the host's immune system.

We claim:

1. A hydrogel system comprising a hydrogel core encapsulated with a covalently crosslinked polymer matrix, wherein said matrix comprises a polycation that electrostatically binds with the hydrogel and a polyanion that covalently crosslinks to the polycation, wherein said polyanion comprises electrophilic reactive groups selected from anhydride, azlactone or succinimide groups to yield an immune-compatible matrix, and wherein the hydrogel core consists of an entity selected from cells, therapeutic agents, enzymes and hormones.

2. The system of claim 1 wherein the hydrogel comprises an alginate, agarose or mixtures incorporating an alginate or agarose.

3. The system of claim 1, wherein the amount of each of the polycation and polyanion in the system is an amount sufficient to result in a 1:1 stoichiometric ratio between reactive groups of the polycation and the reactive groups of the polyanion.

4. The system of claim 1, wherein the polycation is a homopolymer or copolymer having primary amine groups.

5. The system of claim 1, wherein the polycation has a molecular weight in the range of about 1-200 kDa.

6. The system of claim 5, wherein the polycation has a molecular weight in the range of 15-60 kDa.

7. The system of claim 1, wherein the polycation is selected from the group consisting of aminoethyl methacrylate, aminopropylmethacrylamide, aminoethyl acrylate, allylamine, vinylamine a copolymer of an amine-containing monomer with one of an acrylamide, hydroxyethyl methacrylate, hydroxypropylmethacrylamide, dimethylacrylamide, poly(ethylene glycol) methacrylate and methacryloyloxyethyl phosphorylcholine, poly-L-lysine, chitosan, polyornithine and polyethyleneimine.

8. The system of claim 4, wherein the polycation is present at a concentration in the range of about 0.02-1%.

9. The system of claim 1, wherein the polyanion is a homopolymer or copolymer comprising anhydride, azlactone or succinimide groups.

10. The system of claim 1, wherein the polyanion has a molecular weight in the range of about 10-2000 kDa.

11. The system of claim 10, wherein the polyanion has a molecular weight in the range of about 20-500 kDa.

12. The system of claim 10, wherein the polyanion is selected from the group consisting of copolymers of maleic anhydride, cyclic anhydride, linear anhydrides, itaconic anhydride, citraconic anhydride and methacrylic anhydride, with a comonomer selected from the group consisting of alkyl vinyl ether, methyl vinyl ether, ethyl vinyl ether, olefins, ethylene olefin, propylene olefin, copolymers of azlactones with acrylic acid or methacrylic acid, copolymers of N-acryloxysuccinimide, N-methacryloxysuccinimide or glycidyl methacrylate with acrylic comonomers, copolymers of vinylazlactones, succinimides and glycidyl methacrylate with hydroxyethyl methacrylate, methoxypoly(ethyleneglycol) methacrylate or acrylamide.

13. The system of claim 1, wherein the cross-linked polymer matrix is about 1-100 micrometers thick.

14. A method of making an immunocompatible hydrogel system as defined in claim 1 comprising the steps of:
  i) contacting the hydrogel solution with an entity to be encapsulated selected from the group consisting of cells, therapeutic agents, enzymes and hormones and a cross-linking agent to form a gel;
  ii) exposing the gel to an aqueous solution comprising the polycation to form a polycation coated hydrogel;
  iii) exposing the polycation coated hydrogel to the polyanion to form the crosslinked matrix; and
  iv) exposing the matrix to conditions which eliminate, or at least reduce, protein binding sites on the matrix.

15. The method of claim 14, wherein the polycation is selected from the group consisting of aminoethyl methacrylate, aminopropylmethacrylamide, aminoethyl acrylate, allylamine, vinylamine a copolymer of an amine-containing monomer with one of an acrylamide, hydroxyethyl methacrylate, hydroxypropylmethacrylamide, dimethylacrylamide, poly(ethylene glycol) methacrylate and methacryloyloxyethyl phosphorylcholine, poly-L-lysine, chitosan, polyornithine and polyethyleneimine.

16. The method of claim 14, wherein the polyanion is selected from the group consisting of copolymers of maleic anhydride, cyclic or linear anhydrides, itaconic anhydride, citraconic anhydride, methacrylic anhydride, with a comonomer selected from the group consisting of alkyl vinyl ether, methyl vinyl ether, ethyl vinyl ether, olefins, ethylene olefin and propylene olefin, copolymers of azlactones with acrylic acid or methacrylic acid, copolymers of N-acryloxysuccinimide, N-methacryloxysuccinimide or glycidyl methacrylate with acrylic comonomers, copolymers of vinylazlactones, succinimides or glycidyl methacrylate with hydroxyethyl methacrylate, methoxypoly(ethyleneglycol)methacrylate or acrylamide.

17. The method of claim 14, wherein the matrix is exposed to hydrolysis to essentially eliminate protein binding sites.

18. A system as defined in claim 1, wherein the entity is cells.

19. The method as defined in claim 14, wherein the entity to be encapsulated is cells.

20. A hydrogel system comprising a hydrogel core encapsulated with a covalently crosslinked polymer matrix, wherein said matrix comprises a polycation that electrostatically binds with the hydrogel and a polyanion that covalently crosslinks to the polycation, wherein said polyanion comprises electrophilic hydrolyzed reactive groups selected from anhydride, azlactone or succinimide groups to yield a matrix that comprises less than 1% reactive protein binding sites, and wherein the hydrogel core comprises cells.

* * * * *